United States Patent
Von Töerne et al.

(10) Patent No.: US 9,506,112 B2
(45) Date of Patent: Nov. 29, 2016

(54) INCREASING MULTIPLEX LEVEL BY EXTERNALIZATION OF PASSIVE REFERENCE IN POLYMERASE CHAIN REACTIONS

(75) Inventors: Chrisian Von Töerne, Solingen (DE); Udo Stropp, Haan (DE)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 462 days.

(21) Appl. No.: 13/575,315

(22) PCT Filed: Feb. 4, 2011

(86) PCT No.: PCT/US2011/023662
§ 371 (c)(1),
(2), (4) Date: Oct. 10, 2012

(87) PCT Pub. No.: WO2011/097424
PCT Pub. Date: Aug. 11, 2011

(65) Prior Publication Data
US 2013/0040843 A1    Feb. 14, 2013

Related U.S. Application Data

(60) Provisional application No. 61/301,651, filed on Feb. 5, 2010.

(51) Int. Cl.
*C12Q 1/68* (2006.01)
*C12P 19/34* (2006.01)

(52) U.S. Cl.
CPC .................................... *C12Q 1/686* (2013.01)

(58) Field of Classification Search
CPC ............. G01N 21/6428; G01N 33/52; G01N 2021/6428; G01N 2021/6439; C12Q 1/6806; C12Q 1/6851; C12Q 1/6853
See application file for complete search history.

(56) References Cited

U.S. PATENT DOCUMENTS

| | | |
|---|---|---|
| 2006/0019398 A1 | 1/2006 | Corson et al. |
| 2008/0018896 A1 | 1/2008 | Scott et al. |
| 2008/0018898 A1 | 1/2008 | Gunstream et al. |
| 2009/0047679 A1 | 2/2009 | Shain et al. |
| 2010/0015611 A1 | 1/2010 | Webster et al. |
| 2013/0040843 A1* | 2/2013 | Von Toerne ........... C12Q 1/686 506/9 |

OTHER PUBLICATIONS

Potter et al. Poster presented at ABRF 2002: Biomolecular Technologies: Tools for Discovery in Proteomics and Genomics, Austin, TX, Mar. 2002; poster P13-S.*
Coleman et al 2007 Biotechniques 43: 517-519.*
ABI Prism 7700 Sequence Detection System Installation Manual, 2001 Applied Biosystem, 56 pages.*
International Search Report, PCT/US2011/23662, Apr. 12, 2012.

* cited by examiner

*Primary Examiner* — David Thomas

(57) ABSTRACT

Methods for increasing multiplex level by externalization of a passive reference in polymerase chain reactions (PCR) are provided. An exemplary method comprises providing a first mastermix including a passive fluorescence dye in at least a first well of a plate; providing a second mastermix including an active fluorescence dye in at least a second well of the plate; wherein the passive fluorescence dye and the active fluorescence dye emit a same spectrum and an intensity of the spectrum is adapted to be measured; and wherein the first mastermix is devoid of an active fluorescence dye emitting the same spectrum and the second mastermix is devoid of the passive fluorescence dye emitting the same spectrum. Numerous other aspects are provided.

22 Claims, 7 Drawing Sheets

INCREASING MULTIPLEX LEVEL BY EXTERNALIZATION OF PASSIVE REFERENCE IN POLYMERASE CHAIN REACTIONS

FIELD OF THE INVENTION

The present invention relates to the field of molecular biology and biochemical processes, and more specifically to methods for increasing multiplex level in polymerase chain reactions (PCR).

BACKGROUND

Detecting and identifying minute amounts of DNA or, after reverse transcription, RNA, from a sample is important for medical diagnostic purposes, routine care, research, etc. For example, the DNA may be from a bacteria or virus and indicate the presence and quantity thereof in the sample. One widely known method for detection and identification of minute amounts of DNA or RNA, miRNA, siRNA or other types of nucleic acid fragments, for example, is a polymerase chain reaction (hereinafter "PCR"). Through a series of cycles, the PCR exponentially amplifies or increases the amount of a specific target region of the nucleic acid, facilitating ease of analysis. Geneticists and medical researchers, for example, use PCR to determine if certain genes are present in a DNA sample and to create enough DNA to analyze the sequence. While PCR may be applied to DNA and, after potential additional process steps, RNA and other fragments of nucleic acids, hereinafter, it will be described with respect to DNA.

As known in the art, during a PCR procedure, a reagent or mastermix including a double strand of DNA, for example, may be divided into a plurality of wells on microtiter plates. The mastermix may include a suspension of ingredients, such as samples of DNA, selected DNA primer strands, DNA elements, enzymes, and fluorescent dye, for example. Other ingredients may be included in the mastermix. Multiple reactions typically occur in parallel on these plates and may detect multiple target regions of DNA simultaneously in the same well (multiplex). The reagent may be heated to denature, or separate into single strands, the target region of DNA. The reagent may then be cooled, allowing the primers to anneal or pair to their complementary sequence. The primers may be designed to bracket the target region of DNA to be amplified. The temperature may then be increased, allowing polymerase, such as Taq polymerase, for example, to attach at each priming site and extend (synthesize) a new DNA strand. This method may be repeated a number of times or cycles allowing the number of DNA strands to build up. As the method progresses through each cycle, the polymerase and primers may be reused, making copies of the DNA strands starting at the sequence where the primers bind. Because the sequence of the primers is known, the researcher may determine if the result of the PCR is positive or negative, or draw conclusions of the initial quantity of target DNA in the sample considered.

During standard PCR, the result of the PCR may be determined at the end of all the cycles by running the PCR mixture on a gel and visualizing the size of the DNA amplified, for example. During real-time PCR, the result of the PCR may be determined as the reaction progresses in real time. Two common methods for detection of products in real-time PCR are: (1) non-specific fluorescent dyes that bind with any double-stranded DNA and, (2) sequence-specific DNA probes that are labeled with a fluorescent reporter dye, which permits detection only after hybridization of the probe with its complimentary DNA target region. With non-specific fluorescent dyes, the DNA-binding dye binds to all double-stranded DNA in PCR, causing fluorescence of the dye. An increase in DNA product during PCR therefore leads to an increase in fluorescence intensity and is measured at each cycle. With the sequence-specific probes, the fluorescent reporter probe only detects the DNA containing the probe sequence; therefore, use of the reporter probe significantly increases specificity, and enables quantification even in the presence of non-specific DNA amplification. Fluorescent probes can be used in multiplex assays, for example, for detection of several target regions of DNA in the same reaction, based on specific probes with different-colored labels. Each color (detection/emission wave length) may be associated with a specific dye, and may be referred to as a dye. Amplification/detections devices may be equipped with different filters or other optical/electronic devices to separate different optical spectral ranges, i.e. the spectral range of the respective probe label. The number of target regions of DNA in the initial (unamplified) sample may be estimated by certain properties of the curve of detected fluorescence against cycle number, e.g., by comparison of the fluorescence intensity with a threshold intensity. In some instances the threshold intensity may be predefined, or may be based on the results at hand, for example. The cycle at which the fluorescence from a sample crosses the threshold is called the cycle threshold ($C_t$).

"Dye" and "channel" in this application are partly used interchangeably meaning that a certain dye can only be measured in one channel, or a one-to-one relationship exists, but, generally speaking, as a channel is typically a filter used to detect an emitted spectrum, different dyes can be measured in one channel like HEX, VIC JOE.

The inventors of the present invention have determined that existing problems with conventional real-time PCR specific target detection methods are:

The influence of reagent pipetting variations. For example, pipetting different amounts of sample into each of the wells in a single plate.

The variation that is observed when comparing the quantity of identical samples on different instruments; and The variation or invalidation of the quantity due to specific non-optimal characteristics in the amplification/detection method, e.g. by stray light, temperature differences, differences from well to well in the plastics material (PCR plate and sealing) etc.

These problems may cause systematically incorrect values for target DNA concentrations, which may lead to incorrect, disadvantageous diagnostic results, for example.

Two conventional ways to avoid at least some of the aforementioned problems are:

The use of adaptive algorithms to standardize and remove the background level, the result of which may be referred to as dR. The initial quantity of target region DNA is determined by comparing dR to a threshold value which may yield a $C_t$ value (fractional cycle number for the point where fluorescence signal passes threshold). The threshold value is usually shared by all wells in the same channel on the same plate, or even pre-defined and used across multiple plates or even instruments. While this method adequately captures variations in reagent pipetting and some of the variations incurred by different instruments, the inventors of the present invention have determined that this method does not detect or eliminate at least some of the non-optimal features specific to this reaction run (e.g. cycle-dependent variation).

The use of normalization of the fluorescence signal of an actively reporting dye (a fluorescence color indicating a target DNA region) by the fluorescence of a passive or reference dye (another dye which is not used for target DNA region detection) in the same well, preferably per-cycle. After normalization, the background noise is estimated and removed or cleared. The resulting value is called the normalized intensity, or dRn. This method accounts for pipetting variations in reagents used (all reagents are at a constant ratio in the reagent mastermix, so if more is pipetted into a well of the plate, the ratio of the active and passive signal will remain unchanged), is relatively reproducible between different instruments, and may be able to detect and eliminate specific non-optimal characteristics of the amplification/detection run itself and thereby may produce reliable data.

Conventional multiplex PCR includes multiple primer sets within a single PCR mixture to produce amplified regions of varying sizes that are specific to different DNA sequences. By targeting multiple regions of interest at once, additional information may be gained from a single test run that otherwise would require several times the reagents and/or more time to perform. However, in multiplex reaction runs involving multiple different dyes, the reaction run may be limited in the number of target DNA regions or regions of interest (ROI) that may be detected. In other words, in many PCR machines a limited number of dyes are available for each reaction run. For example, on the VERSANT kPCR platform offered by Siemens, only 5 dyes are available for quantitative detection of nucleic acids. With the normalization of the fluorescence signal of an actively reporting dye method described above, of these 5 dyes, one of the dyes is used as a passive reference, thereby limiting the number of separately detectable nucleic acids. For example, an HPV (human papilloma virus) assay may include 14 ROIs (plus a cellular control channel) that conventionally may be detectable by 4 dyes in a 5-dye system, as one dye is used as a reference dye. The assay, for example, may be as follows:

CY5: cellular control
HEX: HPV16
ALEXA: HPV18
FAM: HPV33, 35, 51, 52, 56, 31, 39, 68, 45, 58, 59
ROX: passive reference There are presently not enough dyes to detect HPV45 on a separate channel; a signal reported in FAM channel could be due to any of the targets. Thus PCR for HPV45 needs to be run on a separate dye in a different reaction.

It should be noted that while machines providing more than 5 dyes may be available for detecting more types of ROIs, as the number of dyes increases, the distinction between the different wavelengths/fluorescence decreases (e.g. by crosstalk), making identification of ROIs more difficult. Accordingly a need exists for an improved method and apparatus for detecting and determining the number of ROIs in a sample.

SUMMARY OF THE INVENTION

In an aspect of the present invention, a method is provided. The method includes providing a first mastermix including a passive fluorescence dye in at least a first well of a plate; providing a second mastermix including an active fluorescence dye in at least a second well of the plate; wherein the passive fluorescence dye and the active fluorescence dye emit a same spectrum and an intensity of the spectrum is adapted to be measured; and wherein the first mastermix is devoid of an active fluorescence dye emitting the same spectrum and the second mastermix is devoid of the passive fluorescence dye emitting the same spectrum.

In another aspect of the present invention, a method is provided. The method includes providing a first mastermix including a passive fluorescence dye in at least a first well of a plate; providing a second mastermix including two or more active fluorescence dyes in at least a second well of the plate; wherein the passive fluorescence dye emits the same spectrum as one of the active fluorescence dyes and an intensity of the dye is adapted to be measured; and wherein the first mastermix is devoid of an active fluorescence dye emitting the same spectrum and the second mastermix is devoid of the passive fluorescence dye emitting the same spectrum.

Other features and aspects of the present invention will become more fully apparent from the following detailed description, the appended claims, and the accompanying drawings.

BRIEF DESCRIPTION OF THE DRAWINGS

FIGS. 7A and 7B are computer code depicting an algorithm according to some embodiments of the present invention.

DETAILED DESCRIPTION

The present invention provides methods and apparatus for increasing multiplex level by externalization of a passive reference in polymerase chain reactions (PCR). In particular, the present invention provides a method whereby one of the dyes is used both in a passive manner to normalize the data, and in an active manner to detect regions of interest (ROI).

Figure 1:
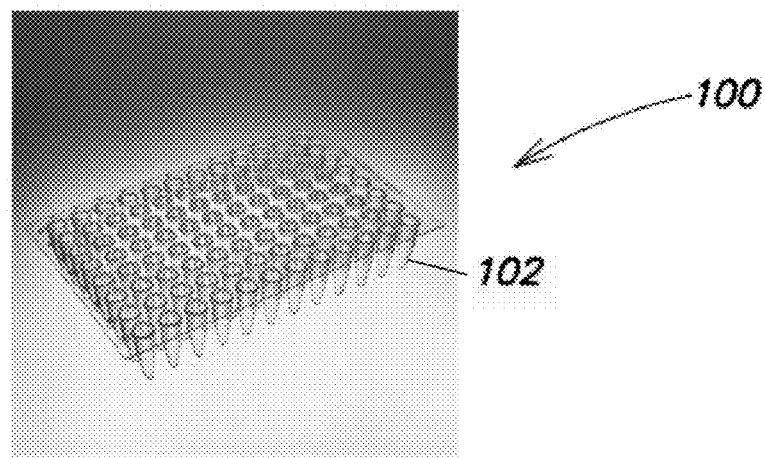
FIG. 1 is a schematic view of a plate including wells according to some embodiments of the present invention.

As described above, a plate 100 (FIG. 1) may include a plurality of wells 102 (FIG. 1). Each well 102 may receive, via pipetting, for example, a specific amount of a mastermix. The mastermix may include a suspension of ingredients, such as samples of DNA, selected DNA primer strands, DNA elements, enzymes, and fluorescent dye, for example. Other ingredients may be included in the mastermix. In some embodiments, the same volume of mastermix may be pipetted into a plurality of the wells 102 of a plate 100. As described above, a fluorescent dye, such as ROX, for example, may be passive or active. While ROX is used as an exemplary dye herein, other suitable dyes, such as CY5, HEX, ALEXA, FAM, JOE, VIC, Yakima Yellow and Atto may be used. Other suitable dyes may be used. "Passive ROX" may refer to free or pure dye that does not change during PCR and is not connected to a probe. More generally, "passive fluorescence dye" may refer to any suitable dye that is free or pure dye that does not change during PCR and is not connected to a probe. Passive ROX does not report amplification, as passive ROX does not participate in PCR. However, since passive ROX remains constant during the PCR, passive ROX may indicate the effects of thermal stress, pipetting variations, and other non-amplification factors that may affect the fluorescence signal. "Active ROX" may refer to ROX dye that is initially connected to a probe. More generally, "active fluorescence dye" may refer to any suitable dye that is initially connected to a probe. A probe contains a sequence of DNA complementary to some sequence specific to the ROI, so that it will easily bind to the ROI. The probe contains a dye (ROX) at one end, and a quencher at the other end. The probe is designed such that when the probe is intact, the quencher suppresses the fluorescent signal. During the extension step of PCR, the polymerase may separate the dye from the quencher, thus setting the dye free and allowing the dye to emit a characteristic fluorescence, which may be detected by a detector when excited. Active ROX signal may indicate the amount of ROI in the mastermix. In the present invention, some wells 102 may receive mastermix containing passive ROX, while other wells of the same plate 100 may receive mastermix containing active ROX. As both the passive ROX and active ROX both use the ROX dye, the dye emits the same spectrum. The data from these different types of wells 102 may be compared to each other, and the data from the active-dye wells 102 is normalized to a mathematical combination of the data from the passive-dye wells 102 and the active wells.

Figure 2:
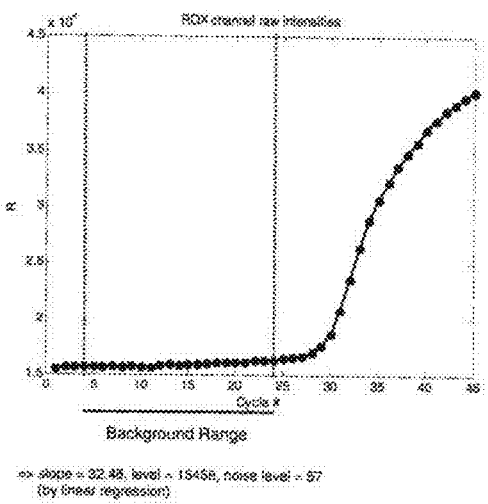
FIG. 2 is a graph depicting active ROX data according to some embodiments of the present invention.

In the active ROX wells 102, a user-defined number of PCR cycles are performed. With each successive cycle more dye is released, thereby providing a fluorescent signal with increasing intensity, as indicated by the graph in FIG. 2. In the beginning cycles, such as cycles 1 to 23, for example, the background may be too great to detect a fluorescent ROX signal (i.e. no significant signal over background, e.g. because noisy measurement obscures signal). However, starting at about cycle number 24, enough active ROX may have been released such that fluorescence may be detected over the background. While the graph in FIG. 2 applies specifically to active ROX, in a multiplex PCR, PCR for different DNA sequences or ROIs may occur in parallel. These different ROIs may be identified by other dyes, such as CY5, HEX, ALEXA and FAM. Other suitable dyes may be used.

Figure 3:
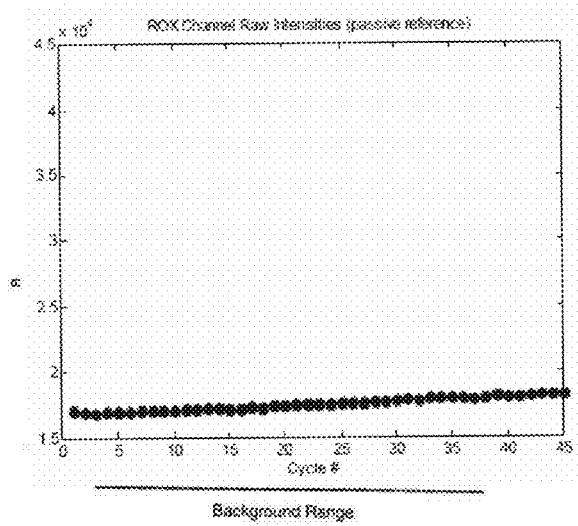
FIG. 3 is a graph depicting passive ROX data according to some embodiments of the present invention.

While PCR occurs in the active ROX wells 102 for ROIs labeled by ROX, as well as ROIs labeled by other dyes, PCR may also occur in the passive ROX wells 102. However, in the passive ROX wells 102, the ROI detected by active ROX in the active ROX wells 102 may not be reported in the ROX channel in the passive ROX wells 102, or may not be detected at all. With the HPV example described above, for example, in the passive ROX wells 102 there may be a PCR amplification occurring for a ROI that is reported by the FAM dye, and ROX acts as the passive dye. As indicated in FIG. 3, for example, with each successive cycle, the intensity of the ROX dye remains approximately constant. In other words, in the passive ROX wells 102, ROX does not increase with fluorescence with each successive PCR cycle.

Figure 4:
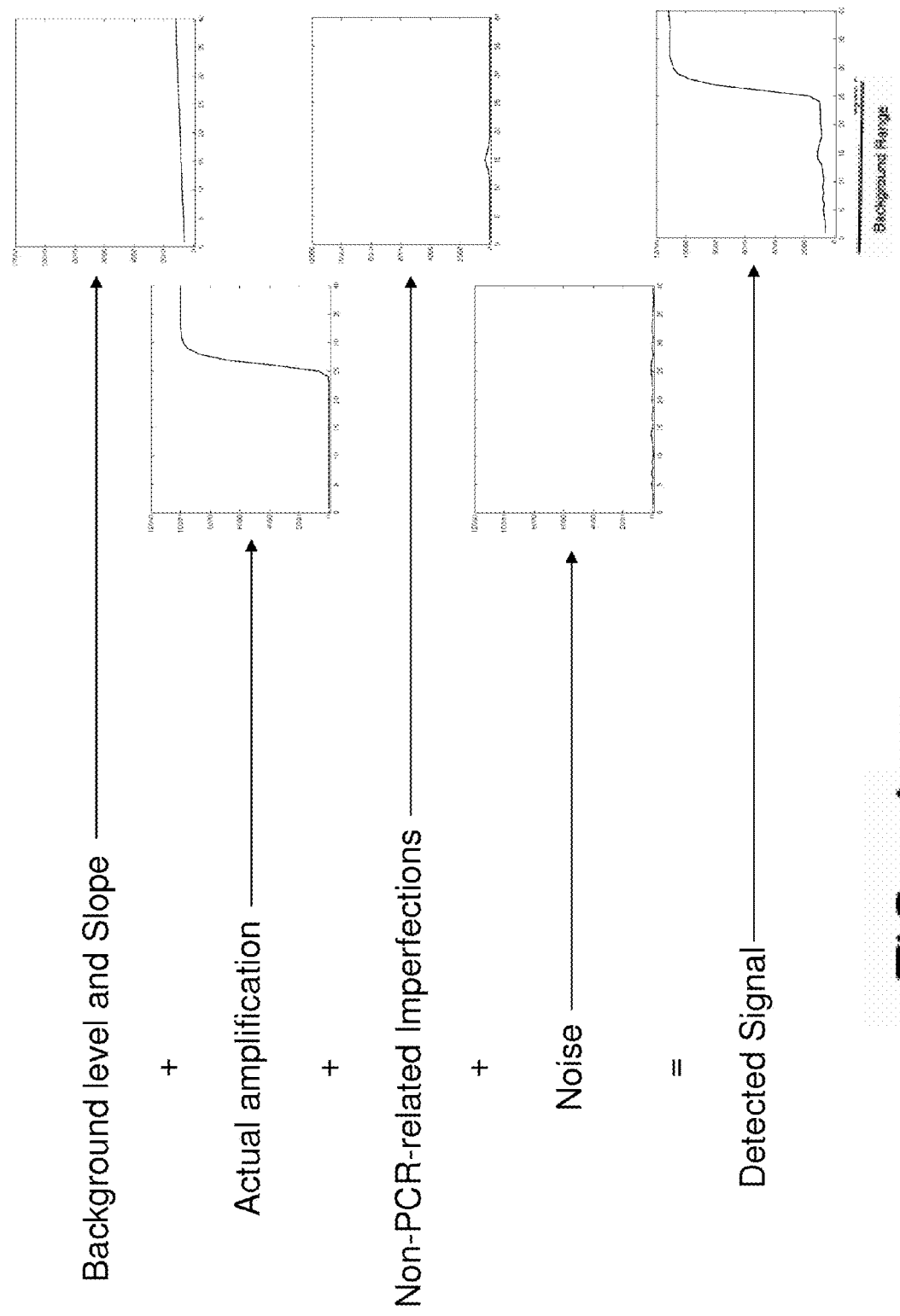
FIG. 4 is a series of graphs depicting factors contributing to the shape of an amplification curve according to some embodiments of the present invention.

FIG. 4 provides a series of five graphs, which may describe some factors that contribute to the shape of an amplification curve. As indicated in FIG. 4, the shape of the data from a detected amplified signal, similar to the shape of the curve in FIG. 2, may be the result of a plurality of features, such as, background level and slope plus the actual amplification plus non-PCR-related imperfections plus noise, for example. Other features may contribute to the shape of the curve.

Figure 5:
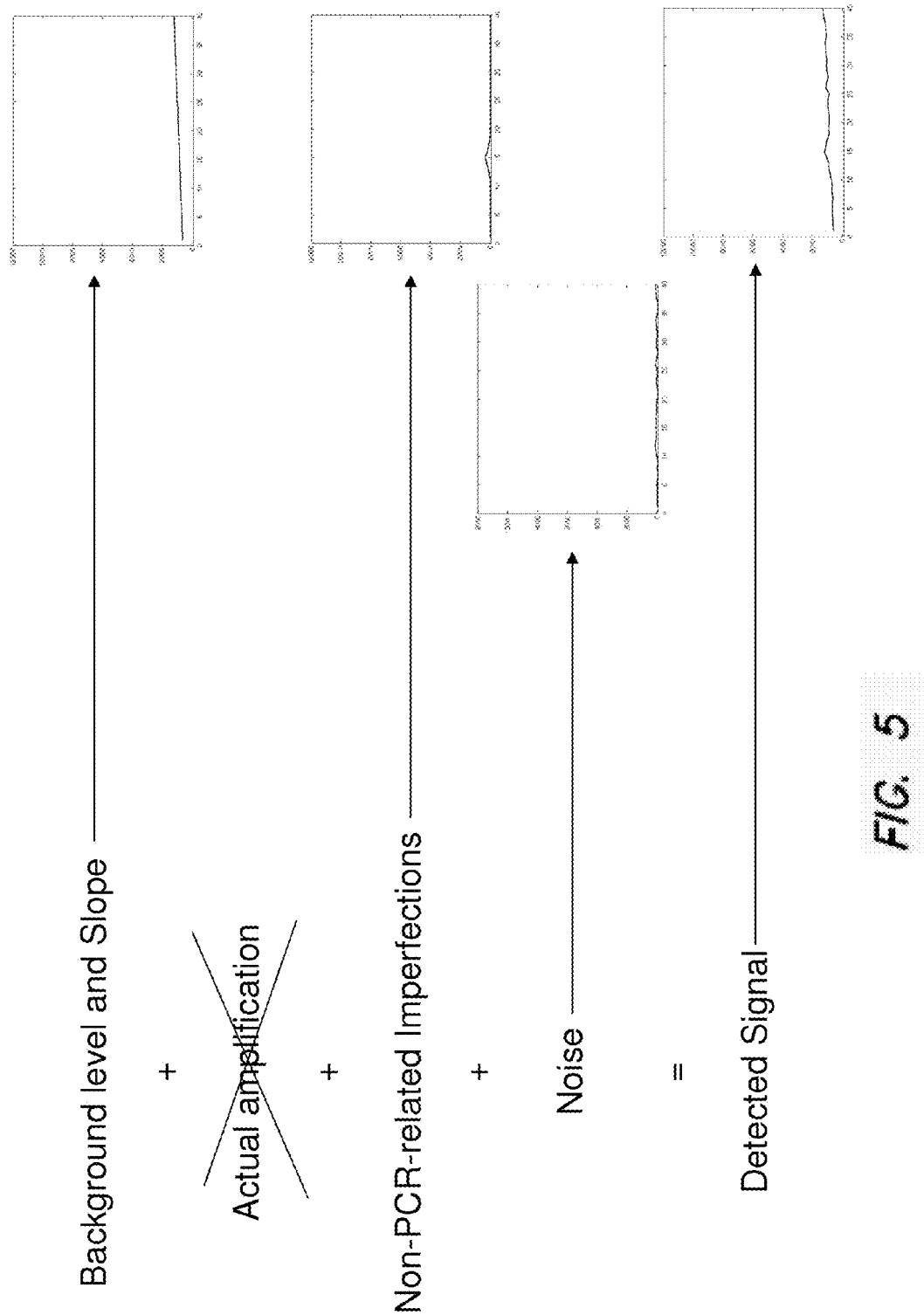
FIG. 5 is a series of graphs depicting factors contributing to the shape of a passive curve according to some embodiments of the present invention.

FIG. 5 provides a series of four graphs, which may describe some factors that contribute to the shape of a passive reference curve. As indicated in FIG. 5, the shape of the data from the detected signal may be the result of a plurality of features, such as, background level and slope plus non-PCR-related imperfections plus noise, for example. As FIG. 5 shows data from a passive reference, it is not detecting amplification, and as such, this factor may not contribute to the shape of the detected signal.

The inventors of the present invention have determined that some of the information provided by the signal intensity data may be considered "plate-wise" information and some of the data may be considered "well-wise" information. Plate-wise information may capture information about the entire PCR, the plate 100, and the instrument, including non-optimal characteristics or non-PCR-related imperfection data. Plate-wise information may be assumed to be redundant in each well 102 on the plate 100, and as such may be successfully estimated from any well 102 on the plate 100. In some embodiments, plate-wise information is specifically estimated solely from the passive reference wells 102, as will be described further below. Well-wise information may be information about the reaction in the specific well 102 under consideration. Well-wise information may account for the mastermix conditions in a well 102, such as pipetting variations, decrease in dye, temperature variability on different portions of the plate etc., for example. The well-wise information may be estimated from the intensity in the initial cycles of a reaction in an actively reporting dye. In some embodiments, the mathematical combination of the well-wise information from active ROX dyes, for example, and plate-wise information from passive ROX dyes, for example, may create an "in silico" signal intensity or virtual reference that can effectively be used for the purpose of signal normalization. As used herein, "In silico" refers to the generation of the reference by means of a mathematical model as part of a computer program rather than genuine measurements in an experiment.

The purpose of normalization may be to cancel or remove the non-PCR related imperfections, as well as pipetting variations from the data. As described above, in conventional multiplex PCR, one dye in each well 102 is used as a reference, while the other dyes in that well 102 are active reporters of amplification. In conventional PCR, the data from each well 102 is normalized, or, in other words, the active dye data is normalized by the reference dye data. After normalization, the non-PCR-related imperfections may be canceled, or no longer considered as affecting the data, as these imperfections may be plate-wise and virtually the same in the reference dyes and active dyes. While the amount of mastermix may vary from well 102 to well 102, the mastermix is the same for different dyes in a single well 102, which may allow for variations in pipetting to be canceled or no longer considered as affecting the data. However, as also described above, the problem with conventional multiplex PCR is that one dye in each well 102 is used as a reference, and therefore is not typically used as an active reporter. Alternatively, if a single dye is used in the same well 102 as a passive and active dye, by acting as an active reference during PCR extension and passive during PCR denaturization, these signals may not be detected and analyzed at the same time.

Figure 6:
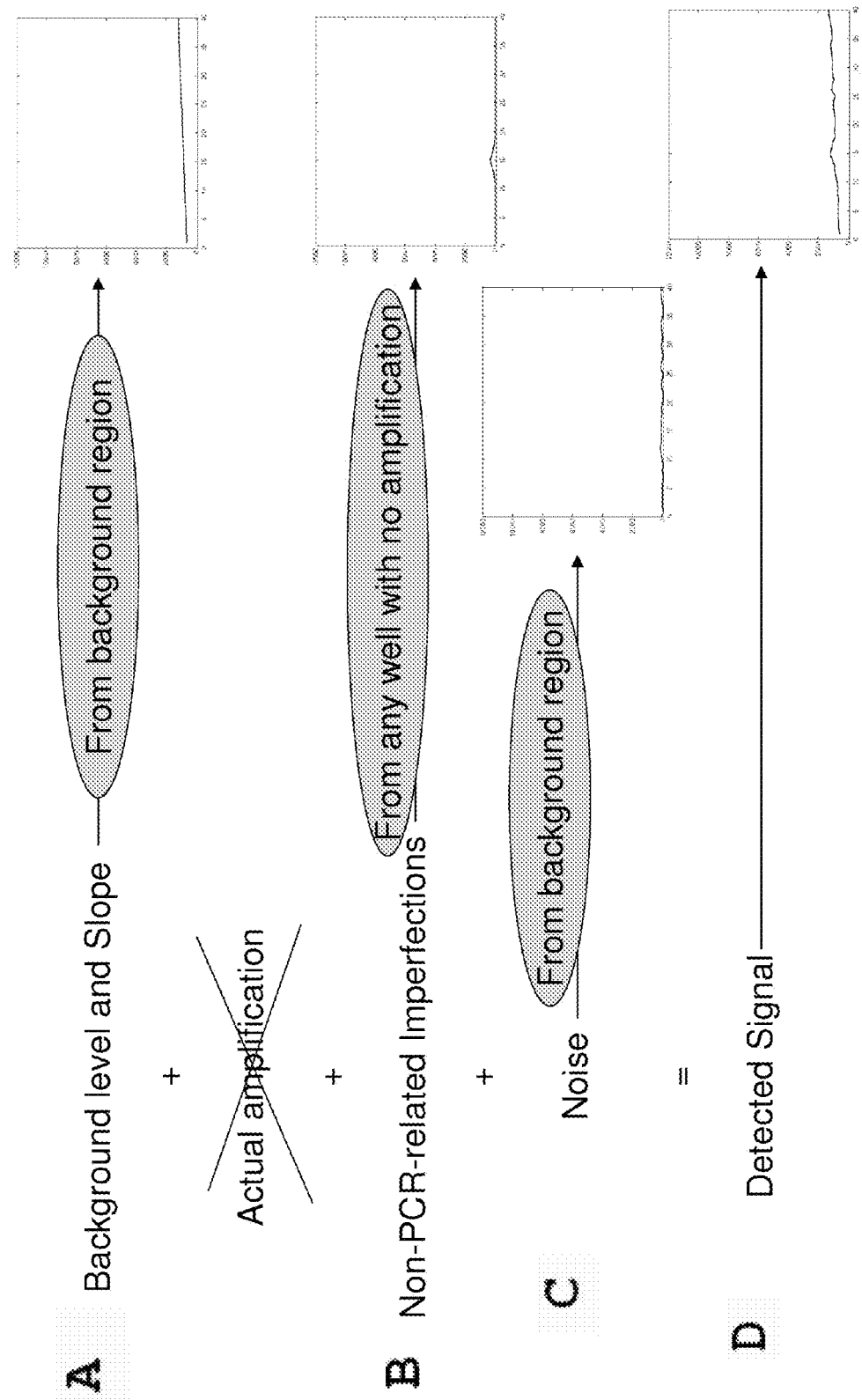
FIG. 6 is a series of graphs depicting a virtual reference according to some embodiments of the present invention.

As described above, in some embodiments of the present invention, the passive reference and active reporter may be in separate wells 102, providing for an additional reporting dye in the active wells 102. The data from the passive ROX wells 102, and in particular, the shape of the passive ROX data, can be used to normalize the data from the active ROX wells 102. In other embodiments of the invention, channels in active wells can be normalized by the measurement of the respective channels in passive wells. To provide the function of the passive reference dye without dedicating a dye in an active well 102 to this purpose, the inventor of the present invention provides a virtual reference. In other words, the virtual reference may be a passive reference model or substitute of a passive reference dye without an actual passive reference dye being present in the active well 102, otherwise referred to as an internal passive reference. As shown graphically in FIG. 6, the virtual reference (D) may be created by extracting the background level/height and slope (A) and noise (C) from the background range/region of the active ROX signal, and non-PCR-related imperfection data from the passive ROX wells (B), as will be further described below. In other words, the background level i.e. height and slope (A) and noise (C) shown in FIG. 6 to create the virtual reference D, may be the background level/height and slope and noise from the background range/region of the active ROX signal as shown in FIG. 4. The data from the background range/region (FIG. 4) of the active reporter signal may be used as a substitute for a passive reference, as the data from these early active cycles may not be dependent on amplification because the amplification may be weak at this point and eclipsed by the background noise. This background level and slope and noise may be considered "well-wise" information. In some embodiments, the well-wise information (e.g. background) may be extracted from every well 102. The well-wise information for active ROX may be extracted by first detecting a range/region on the graph where there is no signal (e.g., background range/region) (FIG. 1) This background range/region may begin with the first cycle and continue to the cycle at which a substantial change in fluorescence is detected. The level, corresponding to pipetting variations, and slope of the data, as well as the noise level, in the background region may then be determined or estimated. The slope, level (e.g. intercept if linear regression is used) and noise level (e.g. derived from residual variation) may be determined or estimated by any suitable means, such as, for example, linear regression. The well-wise information may be the level, slope and noise for the background region.

The remaining data that may be needed to create the passive reference model, and in particular, the non-PCR-related imperfections, may be obtained from any dedicated well 102 where ROX is a passive reference, for example, or a combination thereof. This non-PCR-related imperfection data may be considered "plate-wise" information. In some embodiments, the plate-wise information may be extracted from data of a single well 102. As described above, plate-wise information is assumed to be redundant in each well 102 on the plate 100, and as such, may be extracted for as little as one well 102. The plate-wise information for ROX may be extracted by first selecting a well 102 where ROX is passive. The background region of this data may then be determined. The level and slope of the data in this background region may be estimated, as described above. As described above with respect to FIG. 5, the passive signal may include level and slope data plus noise plus non-PCR-related imperfection data. To isolate just the non-PCR-related imperfection data and noise, the level and slope may be subtracted, or removed from the data of the background region. Then non-PCR-related imperfection data and noise are divided by the noise level, which is well-specific, and therefore varies between passive and active wells. If there are multiple wells 102 with passive ROX, the noise level may effectively be reduced by per-cycle averaging, for example.

A mathematical representation of the passive reference model or "virtual reference" may be:

Virtual reference=$BG+(NPRI/NL_{passive})*NL_{active}$ where
BG at cycle n=Background level+background slope*cycle n. Background level and background slope are estimated from background region of active ROX dye in well 102. Background level has the same unit as the reported fluorescence (usually relative fluorescence units, RFU). Background slope has units RFU/cycle.

NPRI=Non-PCR-related imperfections (from external reference or passive ROX well)

$NL_{passive}$=noise level (from background region of external reference or passive ROX well)

$NL_{active}$=noise level (from background region of active ROX dye in the well we want to normalize)

The virtual reference may then be compared to the data from all of the other active ROX wells 102 on the plate 100 to normalize the active ROX data. In some embodiments, more than one well 102 includes passive ROX. If the plate 100 includes more than one well 102 with passive ROX, the data from all of the passive ROX wells 102 may be combined via, for example, per-cycle averaging, averaging of the model parameters, weighted averaging etc. Any other suitable combination methods may be used. Additionally, in some embodiments, the virtual reference may be used to normalize any of the other channels/dyes in the wells 102 including active ROX.

Figure 7A:
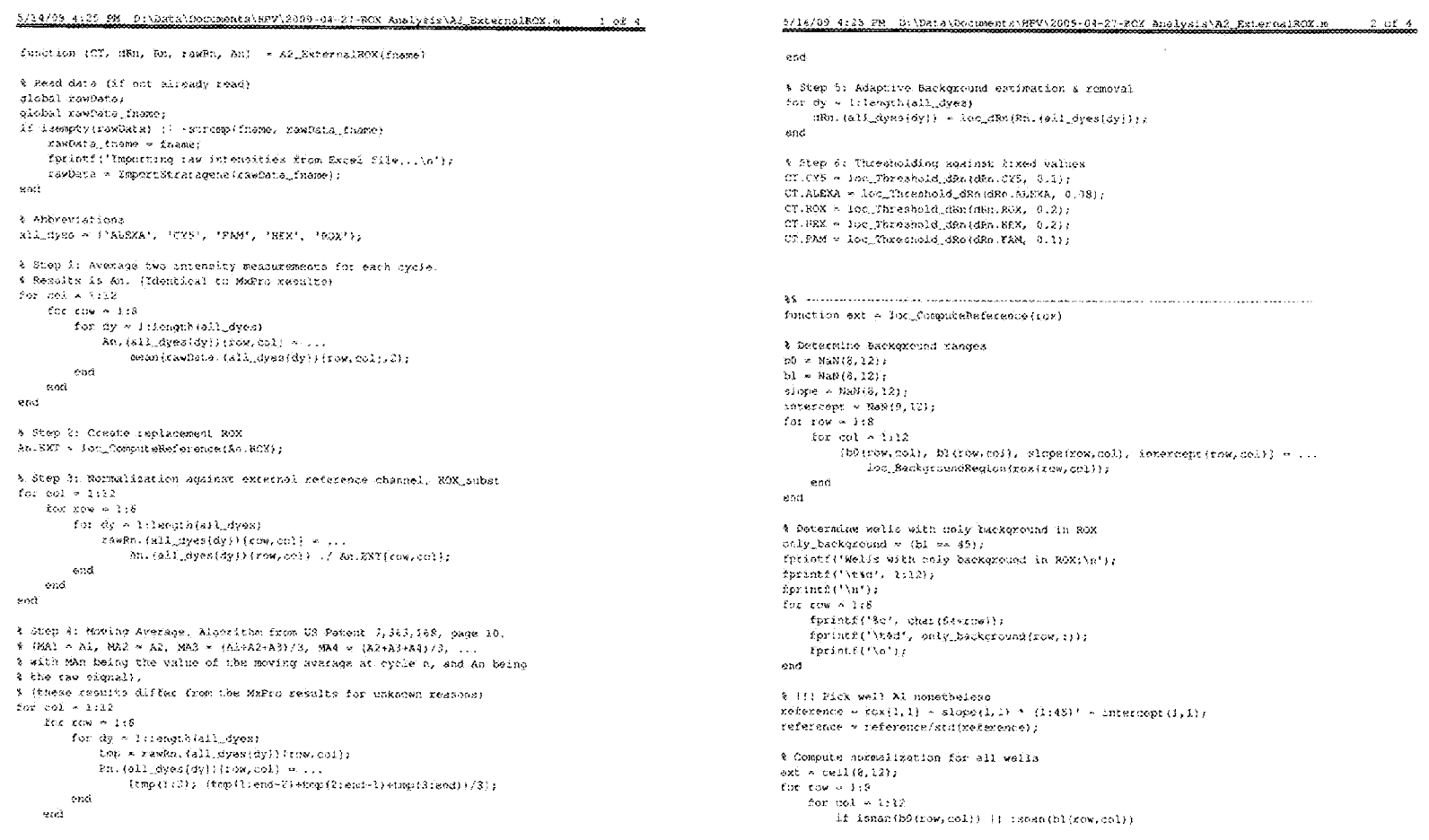
Figure 7B:
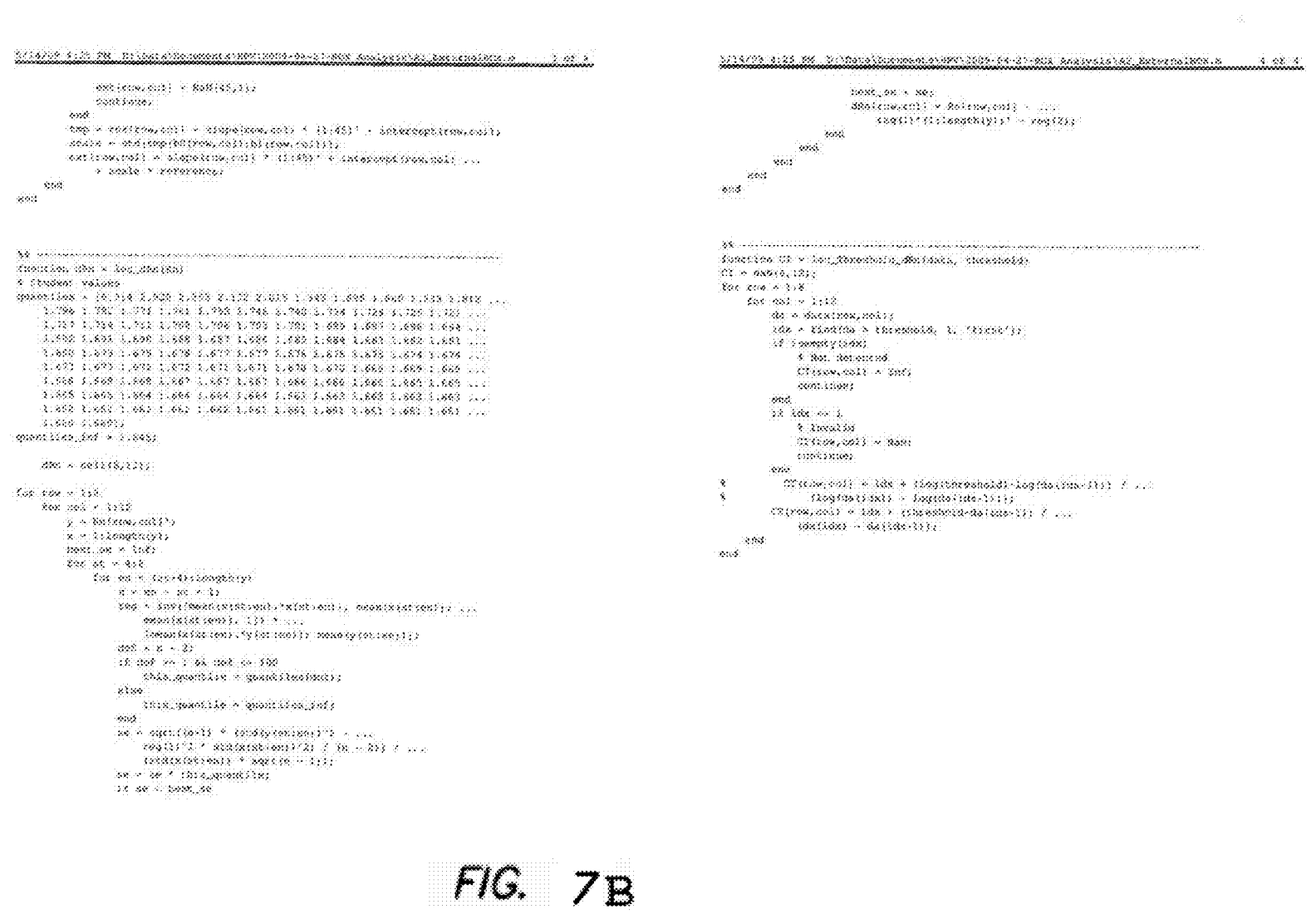

FIGS. 7A and 7B may provide exemplary computer code that may be used to implement the present invention, for example.

The advantage of the present invention is that one dye does not have to be sacrificed as a passive reference dye, but may perform the dual role of acting as a passive and active reference dye. In other words, in the earlier described example regarding the 14-plex HPV assay, ROX may be the dye for HPV45, and a separate PCR run is no longer needed.

The foregoing description discloses only exemplary embodiments of the invention. Modifications of the above disclosed apparatus and method which fall within the scope of the invention will be readily apparent to those of ordinary skill in the art.

Accordingly, while the present invention has been disclosed in connection with exemplary embodiments thereof, it should be understood that other embodiments may fall within the spirit and scope of the invention, as defined by the following claims.

The invention claimed is:

1. A method comprising:
   providing a plate including a plurality of wells;
   providing a first mastermix that emits a first spectrum in at least a first well of the plate, wherein the first mastermix includes a passive fluorescence dye that is a free, non-specific fluorescence dye not coupled to a sequence-specific probe; and
   providing a second mastermix that does not emit the first spectrum in at least a second well of the plate, wherein the second mastermix includes an active fluorescence dye that is initially coupled to a sequence-specific probe that includes a quencher that suppresses fluorescence of the active fluorescence dye; wherein:

the second mastermix is not provided in a same well as the first mastermix;

the active fluorescence dye can be changed to emit the first spectrum by decoupling the active fluorescence dye from the sequence-specific probe; and the first mastermix is devoid of the active fluorescence dye coupled to the sequence-specific probe that includes the quencher and the second mastermix is devoid of the passive fluorescence dye that is not coupled to a sequence specific probe.

2. The method of claim 1 further comprising:
providing the second mastermix including the active fluorescence dye in two or more of the plurality of wells.

3. The method of claim 1 further comprising:
performing a polymerase chain reaction in each of the first and second wells.

4. The method of claim 3 further comprising:
measuring an intensity of the passive and active fluorescence dyes for each cycle of the polymerase chain reaction.

5. The method of claim 4 further comprising:
providing data of the measured intensity of the passive and active fluorescence dyes for each cycle of the polymerase chain reaction.

6. The method of claim 5 further comprising:
extracting well-wise information from the data for the second well containing the active fluorescence dye.

7. The method of claim 6 wherein extracting well-wise information further comprises:
detecting a background region of the data for the second well.

8. The method of claim 7 further comprising:
determining a slope and a level for the background region data for the second well and determining a magnitude of noise for the background region data for the second well.

9. The method of claim 8 further comprising:
extracting plate-wise information from the data for each well containing the passive fluorescence dye.

10. The method of claim 9 further comprising:
generating a mathematical representation of a reference model based on the well-wise information including the slope and the level of the background region data for the second well and the plate-wise information including background region data for the first well with the slope and level of the background region data removed from background region data.

11. The method of claim 10 further comprising:
normalizing the data of the measured intensity from the wells including the second mastermix with the reference model.

12. A method comprising:
providing a first mastermix that emits a first spectrum in at least a first well of a plate, wherein the first mastermix includes a passive fluorescence dye that is a free, non-specific fluorescence dye not coupled to a sequence-specific probe; and
providing a second mastermix that does not emit the first spectrum in at least a second well of the plate, wherein the second mastermix includes two or more active fluorescence dyes that are initially coupled to a sequence-specific probe that includes a quencher that suppresses fluorescence of the active fluorescence dyes; wherein:

the second mastermix is not provided in a same well as the first mastermix;

one of the active fluorescence dyes can be changed to emit the first spectrum by decoupling the active fluorescence dyes from the sequence-specific probe; and the first mastermix is devoid of the active fluorescence dyes coupled to the sequence-specific probe that includes the quencher and the second mastermix is devoid of the passive fluorescence dye that is not coupled to a sequence specific probe.

13. The method of claim 12 further comprising:
providing the second mastermix including the two or more active fluorescence dyes in two or more of the plurality of wells.

14. The method of claim 12 further comprising:
performing a polymerase chain reaction in each of the wells.

15. The method of claim 14 further comprising:
measuring an intensity of the passive and active fluorescence dyes for each cycle of the reaction.

16. The method of claim 15 further comprising:
providing data of the measured intensity of the passive and active fluorescence dyes for each cycle of the polymerase chain reaction.

17. The method of claim 16 further comprising:
extracting well-wise information from the data for each well containing the active fluorescence dyes.

18. The method of claim 17 wherein extracting well-wise information further comprises:
detecting a background region in the data from the second well;
determining a slope and a level in the background region data; and
determining a magnitude of noise in the background region data.

19. The method of claim 18 further comprising:
extracting plate-wise information from the data for each well containing the passive fluorescence dye.

20. The method of claim 19 further comprising:
generating a mathematical representation of a reference model based on the well-wise information including the slope and the level of the background region data for the second well and the plate-wise information including background region data for the first well with slope and level removed from the background region data.

21. The method of claim 20 further comprising:
normalizing the data of the measured intensity from the wells including the second mastermix with the reference model.

22. A method comprising:
providing a plate including a plurality of wells;
providing a first mastermix in at least a first well of the plate, the first mastermix including a fluorescence dye that emits a spectrum, wherein the fluorescence dye is free, non-specific fluorescence dye not coupled to a sequence-specific probe;
providing a second mastermix in at least a second well of the plate, the second mastermix including the fluorescence dye coupled to a sequence-specific probe that includes a quencher that suppresses fluorescence of the fluorescence dye; wherein:
the second mastermix is not provided in a same well as the first mastermix;

the fluorescence dye in the second mastermix is adapted to change when undergoing polymerase chain reactions such that the fluorescence of the fluorescence dye becomes no longer suppressed because polymerase chain reactions cause the fluorescence dye to decouple from the sequence-specific probe that includes the quencher; and before the mastermixes undergo any polymerase chain reactions, the first mastermix is devoid of the fluorescence dye coupled to the sequence-specific probe that includes a quencher and the second mastermix is devoid of the free fluorescence dye not coupled to the sequence-specific probe that includes the quencher;

providing the second mastermix in two or more of the plurality of wells;

performing a polymerase chain reaction in each of the first and second wells;

measuring an intensity of the fluorescence of the mastermixes in the first and second wells for each cycle of the polymerase chain reaction;

providing data of the measured intensity of the mastermixes in the first and second wells for each cycle of the polymerase chain reaction;

extracting well-wise information from the data for the second well;

detecting a background region of the data for the second well; and determining a slope and a level for the background region data for the second well and determining a magnitude of noise for the background region data for the second well.

* * * * *